(12) United States Patent
Kaneda et al.

(10) Patent No.: US 8,507,728 B2
(45) Date of Patent: Aug. 13, 2013

(54) METHOD FOR MANUFACTURING KETONE

(75) Inventors: Kiyotomi Kaneda, Hyogo (JP); Hisashi Sone, Kanagawa (JP)

(73) Assignee: JX Nippon Oil & Energy Corporation, Tokyo (JP)

( * ) Notice: Subject to any disclaimer, the term of this patent is extended or adjusted under 35 U.S.C. 154(b) by 55 days.

(21) Appl. No.: 13/130,881

(22) PCT Filed: Nov. 24, 2009

(86) PCT No.: PCT/JP2009/069773
§ 371 (c)(1),
(2), (4) Date: Aug. 5, 2011

(87) PCT Pub. No.: WO2010/061807
PCT Pub. Date: Jun. 3, 2010

(65) Prior Publication Data
US 2011/0288340 A1    Nov. 24, 2011

(30) Foreign Application Priority Data
Nov. 25, 2008 (JP) .................. 2008-299518

(51) Int. Cl.
C07C 45/34 (2006.01)

(52) U.S. Cl.
USPC ........................................ 568/360; 568/401

(58) Field of Classification Search
USPC ................................................ 568/360, 401
See application file for complete search history.

(56) References Cited

FOREIGN PATENT DOCUMENTS

| | | |
|---|---|---|
| EP | 0 237 108 A1 | 9/1987 |
| JP | 5-148177 A | 6/1993 |
| JP | Hei 05-140020 A | 6/1993 |
| JP | Hei 05-148177 A | 6/1993 |
| JP | 2008-231043 A | 1/1995 |
| JP | Hei 07-017891 A | 1/1995 |
| JP | Hei 07-149685 A | 6/1995 |
| JP | Hei 08-067648 A | 3/1996 |
| JP | 2002-191979 A | 7/2002 |

OTHER PUBLICATIONS

Supplementary European Search Report dated Jun. 12, 2012, issued in corresponding European Application No. 09829055.4.

T. Mitsudome et al., "Development of PdCl2-DMA catalyst system for cocatalyst-free Wacker-type oxidation of various olefins", Abstracts of Papers, 238th ACS National Meeting, Washington, DC, Aug. 16-20, 2009, (Jun. 22, 2009).

International Search Report corresponding with International Application No. PCT/JP2009/069773 dated Feb. 2, 2010.

Howard Alper et al., "Palladium chloride and polyethylene glycol promoted oxidation of terminal and internal olefins", Tetrahedron Letters, vol. 26, No. 19, pp. 2263-2264, 1985.

Takato Mitsudome et al., "Convenient and efficient Pd-catalyzed regioselective oxyfunctionalization of terminal olefins by using molecular oxygen as sole reoxidant", Angewandte Chemie, International Edition, vol. 45, No. 3, pp. 481-485, 2006.

Keiichi Mizumoto et al., "PdC12-DMA Shokubatkei ni yoru Kyoshokubai o Mochiinai Shinki Wacker Hanno no Kaihatsu", The Chemical Society of Japan Koen Yokoshu, vol. 89th, No. 1, p. 536, Mar. 13, 2009.

D.G. Miller, et al., "Improved Method for the Wacker Oxidation of Cyclic and Internal Olefins", J. Org. Chem. vol. 55, No. 9, pp. 2924-2927, 1990.

Takahiro Nishimura et al., "Palladium (II)-catalyzed oxidation of terminal alkenes to methyl ketones using molecular oxygen", J/Chem Society, Perkin Trans., vol. 1, pp. 1915-1918, 2000.

PCT International Preliminary Examination Report on Patentability and Written Opinion of the International Searching Authority in International Application PCT/JP2009/069773. Jul. 5, 2011.

*Primary Examiner* — Sikarl Witherspoon
(74) *Attorney, Agent, or Firm* — Fitch, Even, Tabin & Flannery, LLP

(57) ABSTRACT

A method for manufacturing a ketone includes oxidizing an internal olefin or a cyclic olefin having one carbon-carbon double bond or more at a position other than terminals of a molecule thereof in an amide-based solvent in the presence of water, a palladium catalyst, and molecular oxygen, thereby bonding an oxo group to at least one of the carbon atoms constituting the carbon-carbon double bond, in which the amide-based solvent is represented by the formula $$\underset{R^1}{\overset{O}{\underset{\|}{C}}} - \underset{R^2}{\overset{R^3}{N}} \quad (1)$$

in the formula (1), $R^1$ represents an alkyl group having 1 to 4 carbon atoms, $R^2$ and $R^3$ each independently represent an alkyl group having 1 to 4 carbon atoms or an aryl group, and when $R^1$ and $R^2$ are alkyl groups, $R^1$ and $R^2$ may be bonded to each other to form a ring structure.

8 Claims, No Drawings

METHOD FOR MANUFACTURING KETONE

CROSS-REFERENCE TO RELATED APPLICATIONS

This is the U.S. National Phase application of International Application PCT/JP2009/069773, filed Nov. 24, 2009, and claims priority benefit under 35 U.S.C.§119 based on Japanese Application No. 2008-299518, filed Nov. 25, 2008, the entire disclosures of which applications are hereby incorporated herein by reference.

TECHNICAL FIELD

The present invention relates to a method for manufacturing a ketone by oxidizing an olefin.

BACKGROUND ART

Carbonyl compounds including ketones such as methyl ethyl ketone (MEK), methyl isobutyl ketone (MIBK), and acetone, and aldehydes typified by acetaldehyde are useful as solvents and chemical raw materials, and hence used in various fields. Such carbonyl compounds are generally manufactured by two-step reaction methods in which an alcohol produced by hydrating an olefin is dehydrogenated. Meanwhile, as simpler methods, one-step reaction methods have also been known in which an olefin is directly oxidized.

The Wacker process using a $PdCl_2/CuCl_2$ catalyst has been known as one of the methods for directly oxidizing an olefin. This process is effective for the oxidation of terminal olefins each having a carbon-carbon double bond (hereinafter abbreviated as a "C=C bond") at a terminal of a molecule thereof. However, this process has a problem of a low reactivity when used for oxidation of internal olefins each having a C=C bond at a position other than its terminals. This process also has a problem that if the number of carbon atoms of the olefin is increased, the reaction rate is markedly lowered. For this reason, in the industrial field, the use of the Wacker process is limited to only manufacturing of lower carbonyl compounds such as acetaldehyde and acetone, which are obtained by oxidizing lower terminal olefins.

To solve such problems involved in manufacturing a carbonyl compound by direct oxidation of an olefin, various methods have been proposed. For example, Tetrahedron Letters, 1985, 2263-2264 (NPL 1) discloses a method in which terminal and internal olefins are oxidized by using a palladium catalyst, a copper catalyst, polyethylene glycol, and water.

Japanese Unexamined Patent Application Publication No. Hei 5-140020 (PTL 1) discloses a method for manufacturing a carbonyl compound, in which method an olefin is oxidized in an acidic aqueous solution with molecular oxygen in the presence of palladium, an oxoacid salt of a metal having a redox activity (such as copper or iron), a hydroquinone, and a compound capable of converting the hydroquinone into a quinone (such as iron phthalocyanine, or cobalt tetraphenylporphyrin).

Japanese Unexamined Patent Application Publication No. Hei 5-148177 (PTL 2) discloses a method for manufacturing a carbonyl compound, in which method an olefin is oxidized in a solution containing water and urea in the presence of a catalyst comprising a palladium compound and a copper compound and/or an iron compound.

Japanese Unexamined Patent Application Publication No. Hei 7-17891 (PTL 3) discloses a method for manufacturing a carbonyl compound, in which method an olefin and water are allowed to react with each other in the presence of a palladium compound, a copper compound, and an organic phosphorus compound.

Japanese Unexamined Patent Application Publication No. Hei 7-149685 (PTL 4) discloses a method for manufacturing a carbonyl compound, in which method an olefin and oxygen gas are allowed to react with each other in a solvent of an oxygen-containing compound or a sulfur-containing compound in the presence of a palladium compound, a polyoxoanionic compound, and an iron-containing compound.

J. Org. Chem., 1990, 55, 2924-2927 (NPL 2) discloses a modified Wacker process in which a cyclic or internal olefin and p-benzoquinone are allowed to react with each other in the presence of a palladium catalyst by use of a strong acid. Meanwhile, Japanese Unexamined Patent Application Publication No. Hei 8-67648 (PTL 5) discloses a method for manufacturing a ketone, in which method an olefinic compound is oxidized in the presence of water and a palladium compound by use of p-benzoquinone, and the oxidation reaction is conducted by using a heterogeneous strong acid (for example, an sulfonic acid ion exchanger or the like).

J. Chem. Soc., Perkin Trans. 1, 2000, 1915-1918 (NPL 3) discloses an oxidation reaction of an olefin, using pyridine and 2-propanol, in toluene in the presence of palladium acetate.

Japanese Unexamined Patent Application Publication No. 2002-191979 (PTL 6) discloses a method for manufacturing a ketone, in which method an alkene is oxidized with molecular oxygen in the presence of an oxidation catalyst comprising a palladium compound, a heteropolyacid, and a strong acid.

Japanese Unexamined Patent Application Publication No. 2008-231043 (PTL 7) discloses a method for manufacturing a ketone, in which method an olefin is allowed to react with molecular oxygen in the presence of a palladium source, a mesoporous silicate, water, and a protonic acid.

However, the conventional methods for manufacturing a carbonyl compound are not yet sufficiently satisfactory methods for manufacturing a ketone at a high yield and a high selectivity by oxidizing an internal olefin or a cyclic olefin.

Meanwhile, Angew. Chem. Int. Ed., 2006, 45, 481-485 (NPL 4) discloses a method for manufacturing a ketone, in which method molecular oxygen is used as a reoxidizing agent when a terminal olefin is oxidized in a polar solvent such as N,N-dimethylacetamide in the presence of a palladium catalyst.

CITATION LIST

Patent Literature

PTL 1: Japanese Unexamined Patent Application Publication No. Hei 5-140020
PTL 2: Japanese Unexamined Patent Application Publication No. Hei 5-148177
PTL 3: Japanese Unexamined Patent Application Publication No. Hei 7-17891
PTL 4: Japanese Unexamined Patent Application Publication No. Hei 7-149685
PTL 5: Japanese Unexamined Patent Application Publication No. Hei 8-67648
PTL 6: Japanese Unexamined Patent Application Publication No. 2002-191979
PTL 7: Japanese Unexamined Patent Application Publication No. 2008-231043

Non Patent Literature

NPL 1: D. J. H. Smith et al., Tetrahedron Letters, 1985, 2263-2264
NPL 2: D. D. M. Wayner et al., J. Org. Chem., 1990, 55, 2924-2927
NPL 3: S. Uemura et al., J. Chem. Soc., Perkin Trans. 1, 2000, 1915-1918
NPL 4: K. Kaneda et al., Angew. Chem. Int. Ed., 2006, 45, 481-485

SUMMARY OF INVENTION

Technical Problem

The present invention has been made in view of the above-described problems of the conventional techniques, and an object of the present invention is to provide a method which makes it possible to oxidize an internal olefin or a cyclic olefin so that a corresponding ketone can be manufactured at a high yield and a high selectivity.

Solution to Problem

The present inventors have earnestly studied to achieve the above object. As a result, the present inventors have found that when an internal olefin or a cyclic olefin having one carbon-carbon double bond or more at a position other than terminals of a molecule thereof is oxidized by use of a specific amide-based solvent in the presence of a palladium catalyst, water, and molecular oxygen, a ketone which corresponds to the internal olefin or the cyclic olefin, and which has been difficult to manufacture at a high yield and a high selectivity by the conventional methods can be manufactured at a high yield and a high selectivity. This finding has led to the completion of the present invention.

Specifically, a method for manufacturing a ketone of the present invention comprises:

oxidizing an internal olefin or a cyclic olefin having one carbon-carbon double bond or more at a position other than terminals of a molecule thereof in an amide-based solvent in the presence of water, a palladium catalyst, and molecular oxygen, thereby bonding an oxo group to at least one of the carbon atoms constituting the carbon-carbon double bond, the amide-based solvent being represented by the formula (1):

[Chem. 1]

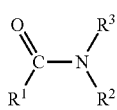

(1)

(in the formula (1), $R^1$ represents an alkyl group having 1 to 4 carbon atoms, $R^2$ and $R^3$ each independently represent an alkyl group having 1 to 4 carbon atoms or an aryl group, and when $R^1$ and $R^2$ are alkyl groups, $R^1$ and $R^2$ may be bonded to each other to form a ring structure). A concentration of the palladium catalyst is preferably 0.002 to 1 mol/L.

In the method for manufacturing a ketone of the present invention, the preferred internal olefin or the preferred cyclic olefin is a compound represented by the following formula (2):

[Chem. 2]

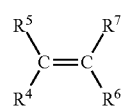

(2)

(in the formula (2), $R^4$ to $R^7$ each independently represent one selected from the group consisting of a hydrogen atom, alkyl groups, alkenyl groups, and aryl groups; at least one of $R^4$ and $R^5$ is any one of an alkyl group, an alkenyl group, and an aryl group; at least one of $R^6$ and $R^7$ is any one of an alkyl group, an alkenyl group, and an aryl group; when $R^4$ and $R^6$ are an alkyl group or an alkenyl group, $R^4$ and $R^6$ may be bonded to each other to form a ring structure; and when $R^5$ and $R^7$ are an alkyl group or an alkenyl group, $R^5$ and $R^7$ may be bonded to each other to form a ring structure). More preferably, the internal olefin or the cyclic olefin does not have any carbon-carbon double bond at the terminals of the molecule thereof.

In addition, the preferred palladium catalyst is at least one palladium compound selected from the group consisting of palladium halides and nitrile complexes of palladium halides. The preferred amide-based solvent is at least one selected from the group consisting of N,N-dimethylacetamide and N-methyl-2-pyrrolidone.

Note that, it is not exactly clear why the manufacturing method of the present invention makes it possible to oxidize the internal olefin or the cyclic olefin so that a desired corresponding ketone can be manufactured at a high yield and a high selectivity. However, the present inventors presume as follows. Specifically, since internal olefins and cyclic olefins have a lower reactivity than those of terminal olefins, the oxidation reaction thereof does not proceed sufficiently in the conventional Wacker process. As a result, the yield of the corresponding ketone is decreased. In addition, it is also presumed that, in the conventional Wacker process, since an isomerization reaction of an internal olefin occurs during the oxidation of the internal olefin, the production amount of the ketone corresponding to the internal olefin is reduced, which also leads to a decrease in the selectivity to the desired corresponding ketone.

In contrast, it is presumed that, in the method for manufacturing a ketone of the present invention, since it is possible to use molecular oxygen alone as the reoxidizing agent without copper, the Wacker reaction of an internal olefin or a cyclic olefin, which has a lower reactivity than those of terminal olefins, can proceed efficiently, so that the yield of the corresponding ketone is increased. It is also presumed that, in the method for manufacturing a ketone of the present invention, since no isomerization reaction of the internal olefin occurs during the oxidation of the internal olefin, the selectivity to the desired corresponding ketone is increased.

Advantageous Effect of Invention

According to the present invention, it is possible to oxidize an internal olefin or a cyclic olefin so that a corresponding ketone can be manufactured at a high yield and a high selectivity.

DESCRIPTION OF EMBODIMENTS

Hereinafter, the present invention will be described in detail on the basis of preferred embodiments thereof. A method for manufacturing a ketone of the present invention comprises:

oxidizing an internal olefin or a cyclic olefin having one carbon-carbon double bond or more at a position other than terminals of a molecule thereof in an amide-based solvent in the presence of water, a palladium catalyst, and molecular oxygen, thereby bonding an oxo group to at least one of the carbon atoms constituting the carbon-carbon double bond, the amide-based solvent being represented by the formula (1):

[Chem. 3]

(1)

(in the formula (1), $R^1$ represents an alkyl group having 1 to 4 carbon atoms, $R^2$ and $R^3$ each independently represent an alkyl group having 1 to 4 carbon atoms or an aryl group, and when $R^1$ and $R^2$ are alkyl groups, $R^1$ and $R^2$ may be bonded to each other to form a ring structure).

<Olefin>

The olefin used in the present invention is an internal olefin or a cyclic olefin having one carbon-carbon double bond or more at a position other than terminals of a molecule thereof. In the present invention, any olefin having a carbon-carbon double bond at its terminal, or any olefin having no such a bond can be used as the internal olefin or the cyclic olefin, as long as the olefin has one carbon-carbon double bond or more at an internal position in a molecule thereof.

The olefin as described above is preferably a compound represented by the following formula (2):

[Chem. 4]

(2)

(in the formula (2), $R^4$ to $R^7$ each independently represent one selected from the group consisting of a hydrogen atom, alkyl groups, alkenyl groups, and aryl groups; at least one of $R^4$ and $R^5$ is any one of an alkyl group, an alkenyl group, and an aryl group; at least one of $R^6$ and $R^7$ is any one of an alkyl group, an alkenyl group, and an aryl group; when $R^4$ and $R^6$ are an alkyl group or an alkenyl group, $R^4$ and $R^6$ may be bonded to each other to form a ring structure; and when $R^5$ and $R^7$ are an alkyl group or an alkenyl group, $R^5$ and $R^7$ may be bonded to each other to form a ring structure).

The alkyl group and the alkenyl group may be linear, branched, or cyclic. In addition, the number of the carbon atoms of the alkyl group is preferably 1 to 12, and more preferably 4 to 12. Moreover, a hetero atom may be further included, unless the effect of the present invention is impaired. The position of the C=C bond in the alkenyl group is not particularly limited, and may be at a terminal of the alkenyl group, or at an internal position thereof. For example, an olefin having a C=C bond at a terminal of the alkenyl group is a polyene having C=C bonds at terminal and internal positions of a molecule thereof. An olefin having a C=C bond at an internal position of the alkenyl group is a polyene having two or more C=C bonds at internal positions of a molecule thereof. Examples of the aryl group include a phenyl group, a methylphenyl group, and a benzyl group. The aryl group may include a hetero atom, unless the effect of the present invention is impaired.

In addition, $R^4$ and $R^6$, and/or, $R^5$ and $R^7$ may be bonded to each other to form a ring structure. Examples of such a ring structure include cyclic olefins such as cycloalkenes and cycloalkadienes. In such a case, a C=C bond may be present in a moiety other than the ring structure (for example, in $R^5$ and/or $R^7$, when $R^4$ and $R^6$ are bonded to each other to form the ring structure).

Specific examples of such an internal olefin include monoolefins such as 2-butene, 2-pentene, 2-methyl-2-butene, 2-hexene, 3-hexene, 4-methyl-2-pentene, 2-heptene, 3-heptene, 5-methyl-2-hexene, 2-octene, 3-octene, 4-octene, 6-methyl-2-heptene, 2-nonene, 7-methyl-2-octene, 1-phenyl-1-propylene, 1-cyclohexyl-1-propylene, 2-decene, 3-decene, 4-decene, 5-decene, 8-methyl-2-nonene, 1-phenyl-2-butene, 1-cyclohexyl-2-butene, 5-undecene, 6-dodecene, 7-tetradecene, and 8-hexadecene, dienes such as 1,3-pentadiene, 2,4-hexadiene, 2,5-heptadiene, 1,3-octadiene, and 2,4-decadiene, and the like. In addition, isomers, such as cis- and trans-isomers, of these internal olefins can be each used equally.

Specific examples of the cyclic olefin include cycloalkenes such as cyclopentene, cyclohexene, cyclooctene, and cyclodecene, cycloalkadienes typified by cyclooctadiene, those obtained by introducing a substituent group such as an alkyl group or an alkenyl group into these cycloalkenes or cycloalkadienes (for example, vinylcyclohexene, allylcyclohexene), and the like.

These internal olefins and cyclic olefins may be used singly or in combination of two or more kinds. Among these internal olefins and cyclic olefins, preferred are 2-butene, 2-pentene, 2-methyl-2-butene, 2-hexene, 3-hexene, 4-methyl-2-pentene, 2-heptene, 2-octene, 3-octene, 4-octene, 5-decene, 6-methyl-2-heptene, cyclopentene, cyclohexene, and cyclooctene, and more preferred are 3-hexene, 4-octene, 5-decene, and 7-tetra decene, from the viewpoint that the yield of and the selectivity to the corresponding ketone produced are improved.

In the manufacturing method of the present invention, a concentration of the internal olefin or the cyclic olefin is preferably 0.01 to 5 mol/L, and more preferably 0.05 to 1 mol/L. If the concentration of the olefin is lower than the lower limit, the corresponding ketone tends not to be obtained at a high yield. Meanwhile, if the concentration exceeds the upper limit, the corresponding ketone tends not to be manufactured at a high yield because the oxidation reaction of the olefin does not proceed sufficiently.

<Palladium Catalyst>

The palladium catalyst used in the present invention is not particularly limited, as long as the palladium catalyst is a compound containing a palladium atom. Those which have been used in conventional manufacturing of ketones can be each used as the palladium catalyst of the present invention. Specific examples of such a palladium catalyst include inorganic salts of palladium such as palladium sulfate, palladium nitrate, and palladium carbonate, palladium-containing polyoxoanionic compounds such as heteropolyacid palladium salts and isopolyacid palladium salts, palladium halides such as palladium chloride and palladium bromide, palladates such as sodium tetrachloropalladate, sodium tetrabromopalladate, potassium tetrachloropalladate, and potassium tetrabromopalladate, ammine complexes of palladium halides such as tetraamminepalladium dichloride and diamminepalladium tetrachloride, inorganic palladium compounds and complexes such as palladium hydroxide and palladium oxide, organic acid salts of palladium typified by palladium acetate, palladium-containing organic compounds such as palladium acetylacetonate and alkylpalladium compounds, nitrile complexes of palladium halides such as diacetonitrile palladium dichloride and dibenzonitrile palladium dichloride, palladium phosphine complexes typified by tetrakis(triphenylphosphine)palladium, palladium amine complexes typified by palladium ethylenediaminetetraacetate, organic palladium compounds and complexes such as tris(dibenzylideneacetone) dipalladium-chloroform adduct and cyclooctadiene palladium dichloride, active metal palladium such as palladium colloid and highly dispersed palladium metal, and the like. Moreover, anhydrides and hydrates of these compounds can be each used as the palladium catalyst. These palladium catalysts may be singly or in combination of two or more kinds.

Among these palladium catalysts, preferred are palladium halides, and nitrile complexes of palladium halides, and more preferred are palladium halides, from the viewpoint that a yield and a selectivity can be improved in the oxidation reaction of the olefin.

In the present invention, the palladium catalyst may be in a form of being dissolved in the amide-based solvent to be described later, or in a form of being uniformly or non-uniformly dispersed, or in a form of a combination thereof. For example, some of the components of the palladium catalyst (for example, the ligand) may be dissolved in the amide-based solvent, and the rest of the components may be uniformly or non-uniformly dispersed therein.

Moreover, in the present invention, a concentration of the palladium catalyst is preferably 0.002 to 1 mol/L, and more preferably 0.001 to 0.05 mol/L. If the concentration of the palladium catalyst is lower than the lower limit, the corresponding ketone tends not to be manufactured at a high yield because the oxidation reaction of the olefin does not proceed sufficiently. Meanwhile, if the concentration of the palladium catalyst exceeds the upper limit, the oxidation reaction of the olefin tends not to proceed sufficiently because of the formation of an inactive species, Pd black.

<Amide-Based Solvent>

In the present invention, the amide-based solvent represented by the formula (1) is used as a solvent. The use of such an amide-based solvent makes it possible to efficiently reoxidize the palladium catalyst with molecular oxygen.

In the formula (1), $R^1$ represents an alkyl group having 1 to 4 carbon atoms, and $R^2$ and $R^3$ each independently represent an alkyl group having 1 to 4 carbon atoms or an aryl group. When $R^1$ and $R^2$ are alkyl groups, $R^1$ and $R^2$ may be bonded to each other to form a ring structure. Examples of such a ring structure include the pyrrolidone skeleton, the caprolactam skeleton, and the like.

Specific examples of the amide-based solvent used in the present invention include N,N-dimethylacetamide, N,N-diethylacetamide, N,N-dipropylacetamide, N-methyl-N-ethylacetamide, N-butyl-N-phenylacetamide, N,N-dimethylpropanamide, N,N-diethylpropanamide, N-methyl-N-ethylpropanamide, N-methyl-2-pyrrolidone, N-methyl-2-caprolactam, N-ethyl-2-caprolactam, and the like. These solvents may be used singly or in combination of two or more kinds. In addition, in the present invention, the amide-based solvent may be used in combination with other solvents.

Among the amide-based solvents, preferred are N,N-dimethylacetamide and N-methyl-2-pyrrolidone, from the viewpoint that a yield and a selectivity are improved in the oxidation reaction of the olefin.

In the present invention, the amount of the amide-based solvent used is set as appropriate so that the concentrations of the olefin and the palladium catalyst can be within the above-described ranges.

<Water>

In the present invention, the corresponding ketone is manufactured by allowing the olefin to react with water. The amount of water added is not particularly limited, as long as the amount is necessary for the reaction. The amount of water may be set as appropriate according to the kinds of the olefin, the palladium catalyst, and the amide-based solvent to be used, the reaction mode, and conditions thereof. Specifically, the amount of water is preferably 0.5 to 70 parts by volume, and more preferably 1 to 50 parts by volume, relative to 100 parts by volume of the amide-based solvent. If the amount of water added is less than the lower limit, the yield of the corresponding ketone tends to decrease because a sufficient oxidation reaction rate cannot be achieved. Meanwhile, if the amount of water exceeds the upper limit, the activity of the catalyst tends to be lowered because the palladium component deposits or aggregates as palladium metal. Moreover, the yield of the corresponding ketone tends to be decreased, because the low solubility of the olefin in water leads to a decreased contact efficiency of the olefin with the palladium catalyst, so that a sufficient oxidation reaction rate cannot be achieved.

<Oxygen>

In the present invention, the palladium catalyst having been used to oxidize the olefin is reoxidized by using molecular oxygen. At this time, since substantially no co-catalyst such as a copper catalyst is used, the oxidation reaction of the olefin is not inhibited by the copper catalyst, so that the corresponding ketone can be manufactured from the internal olefin or the cyclic olefin at a high yield and a high selectivity.

Examples of the source of the above-described molecular oxygen include oxygen gas, oxygen-enriched air, air, mixture gases of oxygen gas with a diluent gas (these are collectively referred to as "oxygen-containing gases"). Examples of the diluent gas include nitrogen gas, helium gas, argon gas, carbon dioxide, and the like. Nitrogen gas is generally used as the diluent gas.

In the present invention, gases other than these oxygen-containing gases and than the diluent gases can be each used in combination, unless the effect of the present invention is impaired. Moreover, such an oxygen-containing gas may be supplied as a mixture with water, the amide-based solvent, or the like, as needed.

In the present invention, the oxygen-containing gas is preferably supplied at an oxygen pressure of 0.1 to 1 MPa (more preferably 0.3 to 1 MPa). If the oxygen pressure is lower than the lower limit, the corresponding ketone tends not to be manufactured at a high yield because of the formation of an inactive species, Pd black. Meanwhile, if the oxygen pressure exceeds the upper limit, an oxidized by-product tends to be formed in the case of some olefins (for example, in a case of cyclohexene, 2-cyclohexene-1-one is formed where the allylic position is oxidized).

<Oxidation Reaction>

In the method for manufacturing a ketone of the present invention, the ketone is formed by oxidizing the internal olefin or the cyclic olefin in the amide-based solvent in the presence of water, a palladium catalyst, and molecular oxygen, thereby bonding an oxo group (=O) to at least one of the carbon atoms constituting the C=C bond in the olefin. Note that in this description, such a ketone is referred to as a "corresponding ketone."

In the present invention, the mode of the oxidation reaction is not particularly limited, as long as the palladium catalyst and the olefin can be brought into contact with each other. For example, the oxidation reaction can be conducted in any form of gas-liquid reaction and/or liquid-liquid reaction according to the olefin and the palladium catalyst to be used. Moreover, a batch, semi-batch, semi-continuous, or continuous-flow reaction system, or a combination thereof can be employed. In addition, the method for supplying components such as the olefin is not particularly limited, and the components may be supplied in a form of liquid or a form of gas.

Specific examples of the manufacturing method include a batch method in which the oxygen-containing gas and a catalyst solution prepared by mixing the palladium catalyst with the amide-based solvent or a mixture solution obtained by mixing the olefin with the catalyst solution are placed in a batch reactor, and allowed to react with each other; a semi-batch method or a semi-continuous method in which the olefin and the oxygen-containing gas are continuously fed into the catalyst solution, or the oxygen-containing gas is continuously fed into the mixture solution; a continuous-flow method in which the catalyst solution, the olefin, and the oxygen-containing gas are caused to flow simultaneously through a reaction region; and the like.

In the present invention, when the olefin and the oxygen-containing gas are continuously fed into the catalyst solution, the feed rate of the olefin is preferably 10 to 5000 mol/h per mole of palladium. If the feed rate of the olefin is lower than the lower limit, the amount of the corresponding ketone produced per unit time tends to decrease. Meanwhile, if the feed rate exceeds the upper limit, the corresponding ketone tends not to be obtained at a high yield because of the formation of an inactive species, Pd Black. Note that the feed rate of the oxygen-containing gas is adjusted as appropriate so that the oxygen pressure inside the reaction system is within the above-described range.

In the present invention, the reaction temperature for carrying out the oxidation reaction is preferably 0 to 200° C., and more preferably 20 to 100° C. If the reaction temperature is lower than the lower limit, the yield of the corresponding ketone tends to be decreased because of a slow reaction rate. Meanwhile, if the reaction temperature exceeds the upper limit, the selectivity to the corresponding ketone tends to be decreased because a side-reaction, such as isomerization, of the olefin occurs.

Moreover, in the present invention, a concentration of a copper catalyst, which is used in the conventional Wacker process, is preferably 0.03 mol/L or less, more preferably 0.01 mol/L or less, and particularly preferably 0.003 mol/L or less. If the concentration of the copper catalyst exceeds the upper limit, the yield of the corresponding ketone tends to be decreased. From such a viewpoint, in the present invention, it is most preferable to oxidize the internal olefin or the cyclic olefin in the absence of any copper catalyst. In the conventional Wacker process, the copper catalyst accelerates the reoxidation of the palladium catalyst. On the other hand, in a Wacker reaction of an internal olefin or a cyclic olefin, such as the reaction of the present invention, the yield of the corresponding ketone tends to be decreased if a copper catalyst is coexistent. Accordingly, it is presumed that the copper catalyst inhibits an activity of the palladium catalyst in the reaction which would proceed efficiently with molecular oxygen unless the copper catalyst is coexistent.

The corresponding ketone thus obtained can be obtained as any one of a single compound and a mixture, which have a desired purity or composition, by separating and purifying the ketone in a usual manner. In the manufacturing method of the present invention, since few side reactions occur during the oxidation reaction, the unreacted raw material can be recovered and reused for manufacturing the ketone. The amide-based solvent and the palladium catalyst can be also separated and recovered, and then used repeatedly. At this time, the palladium catalyst can be appropriately regenerated, if necessary.

EXAMPLES

Hereinafter, the present invention will be described more specifically on the basis of Examples and Comparative Examples. However, the present invention is not limited to the examples below.

Example 1

Palladium chloride (8.8 mg, 0.05 mmol), dimethylacetamide (DMA, 5 ml), and water (0.5 ml) were placed in a pressure vessel, and heated to 80° C. to dissolve palladium chloride. The obtained solution was transferred to an autoclave reactor. Then, the pressure inside the reactor was raised to 0.9 MPa by supplying oxygen gas thereto, and stirring was conducted for 1 hour. The pressure inside the reactor was released, and trans-4-octene (112 mg, 1.0 mmol) was added thereto. Then, the pressure inside the reactor was raised to 0.6 MPa by supplying oxygen gas thereto, and the oxidation reaction was allowed to proceed at 80° C. for 10 hours.

After completion of the reaction, the product was analyzed by using a gas chromatograph equipped with a FID detector ("GC-2014" manufactured by Shimadzu Corporation, column: KOCL 3 m). As a result, it was found that an oxo group (=O) was bonded to a carbon atom in the C=C bond of trans-4-octene, so that 4-octanone was formed. Accordingly, trans-4-octene was presumably oxidized as shown in the following reaction the formula (I):

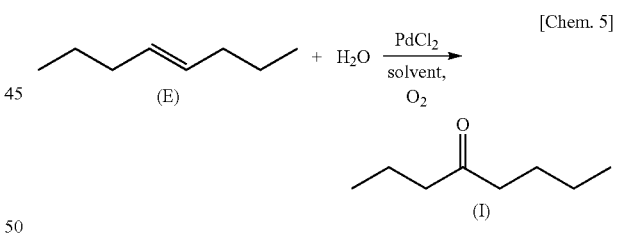

Table 1 shows the yield of 4-octanone based on the amount of trans-4-octene supplied, and the selectivity to 4-octanone with respect to the total amount of the product.

Comparative Examples 1 and 2

Oxidation reactions were conducted in the same manner as in Example 1, except that dimethylacetamide was replaced with dimethylformamide (DMF, 5 ml) or acetonitrile ($CH_3CN$, 5 ml). The products were analyzed in the same manner as in Example 1. As a result, trans-4-octene was presumably oxidized as shown in the above-described reaction formula (I). Table 1 shows the yield of 4-octanone based on the amount of trans-4-octene supplied, and the selectivity to 4-octanone with respect to the total amount of the product.

TABLE 1

| | Solvent | Yield (%) | Selectivity (%) |
|---|---|---|---|
| Ex. 1 | DMA | 91 | >99 |
| Comp. Ex. 1 | DMF | 10 | 90 |
| Comp. Ex. 2 | CH$_3$CN | 14 | 90 |

As is apparent from the results shown in Table 1, it was found that 4-octanone was successfully manufactured at a high yield and a high selectivity, when DMA was used as the solvent (Example 1). Moreover, only 4-octanone was detected as the product, and hence it is presumed that no isomerization reaction of trans-4-octene occurred in the present invention. Meanwhile, when DMF or CH$_3$CN was used as the solvent (Comparative Example 1 or 2), the yield was low, and the selectivity was also low. In addition, 2-octanone and 3-octanone were detected in the product. Accordingly, it is presumed that the oxidation reaction proceeded, after an isomerization reaction of the olefin proceeded.

Examples 2 to 6

Oxidation reactions were conducted in the same manner as in Example 1, except that trans-4-octene was replaced with trans-2-octene (112 mg, 1.0 mmol), trans-3-octene (112 mg, 1.0 mmol), trans-5-decene (140 mg, 1.0 mmol), 7-tetradecene (196 mg, 1.0 mmol), or trans-3-hexene (84 mg, 1.0 mmol) in the respective reactions. The products were analyzed in the same manner as in Example 1. As a result, it was found that an oxo group (=O) was bonded to a carbon atom in the C=C bond of each internal olefin, so that the corresponding ketone was formed. Table 2 shows the yield of the corresponding ketone based on the amount of each internal olefin fed, and the selectivity to the corresponding ketone with respect to the total amount of the product.

Example 7

Oxidation reaction was conducted in the same manner as in Example 1, except that trans-4-octene was replaced with 2-butene (300 mg, 5.3 mmol), that the amount of palladium chloride was changed to 30.4 mg (0.17 mmol), that the amount of dimethylacetamide was changed to 30 ml, that the amount of water was changed to 3.0 ml, and that the reaction time was changed to 4 hours. The products were analyzed in the same manner as in Example 1. As a result, it was found that an oxo group (=O) was bonded to a carbon atom in the C=C bond of 2-butene, so that methyl ethyl ketone was formed. Table 2 shows the yield of methyl ethyl ketone based on the amount of 2-butene supplied, and the selectivity to methyl ethyl ketone with respect to the total amount of the product.

Comparative Example 3 to 5

Table 3 below shows the yields of various ketones manufactured from various internal olefins by the conventional methods, with respect to the amounts of the internal olefins supplied, and the selectivities to the ketones with respect to the amount of all the products. Comparative Example 3 shows the results obtained by the method of D. D. M. Wayner et al. (J. Org. Chem. 1990, 55, 2924), Comparative Example 4 shows the results obtained by the method of D. J. H. Smith et al. (Tetrahedron Letters. 1985, 2263), and Comparative Example 5 shows the results obtained by the method of S. Uemura et al. (J. Chem. Soc., Perkin Trans. 2000, 1, 1915). Note that, in Table 3, Ac represents an acetyl group, BQ represents benzoquinone, and PEG represents polyethylene glycol.

TABLE 2

| | Olefin | Catalyst System | Ketone | Yield (%) | Selectivity (%) |
|---|---|---|---|---|---|
| Ex. 1 | trans-4-octene (E) | PdCl$_2$/DMA | 4-octanone | 91 | >99 |
| Ex. 2 | trans-2-octene (E) | PdCl$_2$/DMA | 2-octanone / 3-octanone | 98 | 63 / 37 |
| Ex. 3 | trans-3-octene (E) | PdCl$_2$/DMA | 3-octanone / 4-octanone | 98 | 55 / 45 |
| Ex. 4 | trans-5-decene (E) | PdCl$_2$/DMA | 5-decanone | 86 | >99 |
| Ex. 5 | 7-tetradecene (E) | PdCl$_2$/DMA | 7-tetradecanone | 70 | >99 |

TABLE 2-continued

| | Olefin | Catalyst System | Ketone | Yield (%) | Selectivity (%) |
|---|---|---|---|---|---|
| Ex. 6 | (E) pent-2-ene | PdCl$_2$/ DMA | pentan-3-one | 80 | >99 |
| Ex. 7 | but-2-ene | PdCl$_2$/ DMA | butan-2-one | 31 | >99 |

TABLE 3

| | Olefin | Catalyst System | Ketone | Yield (%) | Selectivity (%) |
|---|---|---|---|---|---|
| Comp. Ex. 3 | (E) oct-4-ene | Pd(OAc)$_2$/ BQ/ CH$_3$CN/ HClO$_4$ | octan-4-one; octan-3-one; octan-2-one | 87; 11 | 41; 48; 11 |
| Comp. Ex. 4 | (E) long internal olefin | PdCl$_2$/CuCl$_2$/ PEG | ketone | 40 | >99 |
| Comp. Ex. 5 | (E) long internal olefin | Pd(OAc)$_2$/ pyridine/ toluene/ 2-propanol | ketone | 0 | 0 |

As is apparent from the results shown in Tables 2 and 3, when the internal olefin was oxidized by use of a palladium catalyst and benzoquinone (Comparative Example 3), 4-octanone, which was presumably produced through the isomerization reaction of the olefin, was produced, in addition to the ketones formed by bonding an oxo group to the C═C bond of the olefin. Additionally, in the conventional methods, as the alkyl chain became longer, the yield of the corresponding ketone was markedly decreased (Comparative Examples 4 and 5).

In contrast, in the manufacturing methods of the present invention (Examples 1 to 6) where the internal olefins were oxidized in DMA in the presence of PdCl$_2$ catalyst, ketones formed by bonding an oxo group to the C═C bond of the olefins were obtained at a high yield and a high selectivity. In particular, even when the alkyl chain became longer, the marked decrease in the yields of the corresponding ketones was not observed, and the selectivities were extremely high (Examples 4 and 5). Note that it seems that the yield in Example 7 was lower than those in the other Examples. This is due to a small amount of the catalyst and a short reaction time. It may be said, however, that the manufacturing method of the present invention has a sufficient advantage, considering that the oxidation reaction of the internal olefins has hardly proceeded in the conventional methods. Specifically, it may be said that methyl ethyl ketone was manufactured at a high yield and a high selectivity in Example 7, compared with those in the conventional methods, for example, the case where DMF was used as a solvent, and where PdCl$_2$/CuCl$_2$ was used as a catalyst in a concentration comparable to in Example 7.

Example 8

Oxidation reaction was conducted in the same manner as in Example 1, except that trans-4-octene was replaced with cyclohexene (42 mg, 0.5 mmol), and that the amount of palladium chloride was changed to 17.5 mg (0.1 mmol). The products were analyzed in the same manner as in Example 1. As a result, it was found that an oxo group (═O) was bonded to a carbon atom in the C═C bond of cyclohexene, so that cyclohexanone was formed. Table 4 shows the yield of cyclohexanone based on the amount of cyclohexene supplied, and the selectivity to cyclohexanone with respect to the total amount of the product.

Example 9

Oxidation reaction was conducted in the same manner as in Example 8, except that the amount of cyclohexene was changed to 82 mg (1.0 mmol), and that the reaction temperature was changed to 70° C. The products were analyzed in the same manner as in Example 1. As a result, it was found that an oxo group (═O) was bonded to a carbon atom in the C═C bond of cyclohexene, so that cyclohexanone was formed. Table 4 shows the yield of cyclohexanone based on the amount of cyclohexene supplied, and the selectivity to cyclohexanone with respect to the total amount of the product.

Example 10

Oxidation reaction was conducted in the same manner as in Example 8, except that cyclohexene was replaced with cyclopentene (670 mg, 9.8 mmol), that the amount of palladium chloride was changed to 28.7 mg (0.16 mmol), that the amount of dimethylacetamide was changed to 30 ml, that the amount of water was changed to 3.0 ml, and that the reaction time was changed to 4 hours. The products were analyzed in the same manner as in Example 1. As a result, it was found that an oxo group (=O) was bonded to a carbon atom in the C=C bond of cyclopentene, so that cyclopentanone was formed. Table 4 shows the yield of cyclopentanone based on the amount of cyclopentene supplied, and the selectivity to cyclopentanone with respect to the total amount of the product.

TABLE 4

| Olefin | Catalyst System | Ketone | Yield (%) | Selectivity (%) |
|---|---|---|---|---|
| Ex. 8 | cyclohexene | $PdCl_2$/DMA | cyclohexanone | 60 | 70 |
| Ex. 9 | cyclohexene | $PdCl_2$/DMA | cyclohexanone | 73 | 86 |
| Ex. 10 | cyclopentene | $PdCl_2$/DMA | cyclopentanone | 57 | >99 |

As is apparent from the results shown in Table 4, it was found that the corresponding ketones were also successfully manufactured from cyclic olefins at a high yield and a high selectivity. Moreover, comparing Example 8 with Example 9, it was found that the selectivity was improved by lowering the reaction temperature.

Example 11

Oxidation reaction was conducted in the same manner as in Example 1, except that the amount of palladium chloride was changed to 3.5 mg (0.02 mmol), that the amount of trans-4-octene was changed to 56 mg (0.5 mmol), that the oxygen pressure during the oxidation reaction was changed to 0.9 MPa, and that the reaction time was changed to 6 hours. The products were analyzed in the same manner as in Example 1. As a result, it was found that an oxo group (=O) was bonded to a carbon atom in the C=C bond of trans-4-octene, so that 4-octanone was formed. Table 5 shows the yield of 4-octanone based on the amount of trans-4-octene supplied, and the selectivity to 4-octanone with respect to the total amount of the product.

Example 12

Oxidation reaction was conducted in the same manner as in Example 11, except that palladium chloride was replaced with a phenylnitrile complex of palladium chloride ($PdCl_2(PhCN)_2$, 7.7 mg, 0.02 mmol). The products were analyzed in the same manner as in Example 1. As a result, it was found that an oxo group (=O) was bonded to a carbon atom in the C=C bond of trans-4-octene, so that 4-octanone was formed. Table 5 shows the yield of 4-octanone based on the amount of trans-4-octene supplied, and the selectivity to 4-octanone with respect to the total amount of the product.

TABLE 5

| | Catalyst | Yield (%) | Selectivity (%) |
|---|---|---|---|
| Ex. 11 | $PdCl_2$ | 67 | >99 |
| Ex. 12 | $PdCl_2(PhCN)_2$ | 60 | >99 |

Example 13

Oxidation reaction was conducted in the same manner as in Example 1, except that palladium chloride (8.8 mg, 0.05 mmol), copper chloride(II) (3.4 mg, 0.025 mmol), dimethylacetamide (DMA, 5 ml) and water (0.5 ml) were placed in a pressure vessel, that the oxygen pressure was changed to 0.3 MPa, and that the reaction time was changed to 12 hours. The products were analyzed in the same manner as in Example 1. As a result, it was found that an oxo group (=O) was bonded to a carbon atom in the C=C bond of trans-4-octene, so that 4-octanone was formed. Table 6 shows the yield of 4-octanone based on the amount of trans-4-octene supplied, and the selectivity to 4-octanone with respect to the total amount of the product.

Examples 14 and 15

Oxidation reactions were conducted in the same manner as in Example 13, except that the amount of copper chloride(II) added was changed to 6.8 mg (0.05 mmol) or 13.6 mg (0.1 mmol). The products were analyzed in the same manner as in Example 1. As a result, it was found that an oxo group (=O) was bonded to a carbon atom in the C=C bond of trans-4-octene, so that 4-octanone was formed. Table 6 shows the yield of 4-octanone based on the amount of trans-4-octene supplied, and the selectivity to 4-octanone with respect to the total amount of the product.

TABLE 6

| | Cu Species | Added Amount (mmol) | Yield (%) | Selectivity (%) |
|---|---|---|---|---|
| Ex. 1 | — | 0 | 91 | >99 |
| Ex. 13 | $CuCl_2$ | 0.025 | 83 | >99 |
| Ex. 14 | $CuCl_2$ | 0.05 | 74 | >99 |
| Ex. 15 | $CuCl_2$ | 0.1 | 68 | >99 |

As is apparent from the results shown in Table 6, it was found that, although the selectivity to 4-octanone was extremely high irrespective of the amount of copper chloride (II) added, the yield thereof was increased when a smaller amount of copper chloride(II) was added.

Industrial Applicability

As has been described above, the present invention makes it possible to manufacture a corresponding ketone derived from an internal olefin or a cyclic olefin at a high yield and a high selectivity, the corresponding ketone having been difficult to manufacture at a high yield and a high selectivity by the conventional methods.

Accordingly, the method for manufacturing a ketone of the present invention is economically advantageous because of the high yield of the corresponding ketone and the high selectivity thereto, and the ketones obtained by the above-described method are useful as industrial raw materials such as solvents and chemical raw materials.

The invention claimed is:

1. A method for manufacturing a ketone comprising:
oxidizing an internal olefin or a cyclic olefin having one carbon-carbon double bond or more at a position other than terminals of a molecule thereof in an amide-based solvent in the presence of water, a palladium catalyst, and molecular oxygen, in the absence of a co-catalyst, thereby bonding an oxo group to at least one of the carbon atoms constituting the carbon-carbon double bond, the amide-based solvent being represented by the following formula (1):

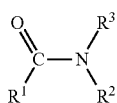
(1)

in the formula (1), $R^1$ represents an alkyl group having 1 to 4 carbon atoms, $R^2$ and $R^3$ each independently represent an alkyl group having 1 to 4 carbon atoms or an aryl group, and when $R^1$ and $R^2$ are alkyl groups, $R^1$ and $R^2$ may be bonded to each other to form a ring structure.

2. The method for manufacturing a ketone according to claim 1, wherein the palladium catalyst is at least one palladium compound selected from the group consisting of palladium halides and nitrile complexes of palladium halides.

3. The method for manufacturing a ketone according to claim 1, wherein the internal olefin or the cyclic olefin is a compound represented by the following formula (2):

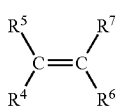
(2)

in the formula (2), $R^4$ to $R^7$ each independently represent one selected from the group consisting of a hydrogen atom, alkyl groups, alkenyl groups, and aryl groups; at least one of $R^4$ and $R^5$ is any one of an alkyl group, an alkenyl group, and an aryl group; at least one of $R^6$ and $R^7$ is any one of an alkyl group, an alkenyl group, and an aryl group;

when $R^4$ and $R^6$ are an alkyl group or an alkenyl group, $R^4$ and $R^6$ may be bonded to each other to form a ring structure; and when $R^5$ and $R^7$ are an alkyl group or an alkenyl group, $R^5$ and $R^7$ may be bonded to each other to form a ring structure.

4. The method for manufacturing a ketone according to claim 1, wherein the internal olefin or the cyclic olefin does not have any carbon-carbon double bond at the terminals of the molecule thereof.

5. The method for manufacturing a ketone according to claim 1, wherein the amide-based solvent is at least one selected from the group consisting of N,N-dimethylacetamide and N-methyl-2-pyrrolidone.

6. The method for manufacturing a ketone according to claim 1, wherein the internal olefin or the cyclic olefin is oxidized in the absence of any copper catalyst.

7. The method for manufacturing a ketone according to claim 1, wherein a concentration of the palladium catalyst is 0.002 to 1 mol/L.

8. A method for manufacturing a ketone comprising:
oxidizing an internal olefin or a cyclic olefin having one carbon-carbon double bond or more at a position other than terminals of a molecule thereof in an amide-based solvent in the presence of water, a palladium catalyst, and molecular oxygen, wherein said oxidizing is conducted essentially free of a co-catalyst to avoid inhibiting said oxidizing, thereby bonding an oxo group to at least one of the carbon atoms constituting the carbon-carbon double bond, the amide-based solvent being represented by the following formula (1):

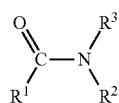
(1)

in the formula (1), $R^1$ represents an alkyl group having 1 to 4 carbon atoms, $R^2$ and $R^3$ each independently represent an alkyl group having 1 to 4 carbon atoms or an aryl group, and when $R^1$ and $R^2$ are alkyl groups, $R^1$ and $R^2$ may be bonded to each other to form a ring structure.

* * * * *